(12) United States Patent
Saleh (10) Patent No.: US 6,623,507 B2
(45) Date of Patent: Sep. 23, 2003

(54) VASCULAR FILTRATION DEVICE

(76) Inventor: Fathy M.A. Saleh, 3001 River Hills La., Midlothian, VA (US) 23113

(\*) Notice: Subject to any disclaimer, the term of this patent is extended or adjusted under 35 U.S.C. 154(b) by 0 days.

(21) Appl. No.: 09/925,984

(22) Filed: Aug. 9, 2001

(65) Prior Publication Data

US 2002/0165575 A1 Nov. 7, 2002

Related U.S. Application Data

(60) Provisional application No. 60/289,069, filed on May 7, 2001.

(51) Int. Cl.[7] .............................................. A61M 29/00
(52) U.S. Cl. ........................................................ 606/200
(58) Field of Search ............................... 606/200, 113, 606/114, 127

(56) References Cited

U.S. PATENT DOCUMENTS

| | | |
|---|---|---|
| 1,641,938 A | 9/1927 | Traut |
| 2,644,586 A | 7/1953 | Cutter ........................ 210/164 |
| RE25,171 E | 5/1962 | Walter ........................ 128/214 |
| 3,827,562 A | 8/1974 | Esmond ...................... 210/304 |
| 4,087,363 A | 5/1978 | Rosemeyer et al. ......... 210/315 |
| 4,170,056 A | 10/1979 | Meyst et al. ............. 29/163.5 F |
| 4,466,888 A | 8/1984 | Verkaart ...................... 210/232 |
| 5,053,008 A | \* 10/1991 | Bajaj .......................... 606/200 |
| 5,108,419 A | 4/1992 | Reger et al. ................. 606/200 |
| 5,357,807 A | 10/1994 | Guckel et al. ................ 73/721 |
| 5,626,605 A | 5/1997 | Irie et al. ..................... 606/200 |
| 5,653,888 A | 8/1997 | Haddock et al. ............. 210/767 |
| 5,984,947 A | 11/1999 | Smith .......................... 606/200 |
| 6,013,093 A | 1/2000 | Nott et al. ................... 606/200 |
| 6,068,645 A | \* 5/2000 | Tu .............................. 606/200 |

\* cited by examiner

*Primary Examiner*—Kevin T. Truong
(74) *Attorney, Agent, or Firm*—Troutman Sanders LLP; Wm. Brook Lafferty (57) ABSTRACT

A vascular filtration device for long-term use to filter a bodily fluid in situ is provided. The vascular filtration device includes a channel for being inserted in-line into a bodily fluid transport passageway and allowing the passage of a quantity of bodily fluid therethrough. A filter is disposed within the channel for removing clots or debris from said quantity of bodily fluid and a sensor is provide for sensing the accumulation of clots and debris on said filter. When clots are detected, the sensor may signal medical professionals that clot removal is necessary, or may automatically trigger the injection of an anticoagulant to dissolve the clots.

38 Claims, 11 Drawing Sheets

VASCULAR FILTRATION DEVICE

RELATED APPLICATIONS AND CLAIM BENEFIT AND PRIORITY

This application claims priority from U.S. Provisional Patent Application No. 60/289,069, filed May 7, 2001.

FIELD OF THE INVENTION

This invention relates to filtration of blood circulating through a patient's body, and more particularly to an apparatus and method for filtering blood flowing through a patient's vein or artery, thereby removing clots and preventing strokes.

BACKGROUND OF THE INVENTION

In Western countries, pulmonary embolisms and strokes are two of the leading causes of death, disability and mental impairment. Generally, pulmonary embolisms and strokes are caused by the formation of clots in a patient's bloodstream and the subsequent migration of those clots to undesirable locations. When migratory clots lodge in a blood vessel, they can occlude the flow of blood to vital areas such as the heart, lungs and brain causing a stroke, collapsed lung, or heart attack. At other times, clots may lodge in blood vessels in the extremities and may block the flow of blood to the hands or feet causing adverse effects.

Various methods have been developed for the treatment of acute clotting incidents and to prevent such incidents before they happen. For example, anticoagulants such as warfarin or heparin may be administered during a stroke incident to prevent or reduce clot formation. However, when used in the long term, these drugs interfere with a patient's clotting ability in response to injury and may have other undesirable side effects. Thus, prolonged use of anticoagulants may not be a suitable treatment for many patients.

Another method sometimes used in the short term to prevent strokes and pulmonary embolisms is the insertion of a filter directly into a patient's blood vessel. For example, U.S. Pat. No. 5,108,419, issued to Reger et al., discloses a filter assembly for placement in the artery of a patient during surgery that includes a collapsible filter assembly positionable in a blood vessel by use of a catheter. Once in place, the assembly is expanded via a rotary mechanism to deploy a series filters having different pore sizes for sequentially removing smaller particles from the patient's blood. At the end of the surgical procedure, the Reger device can be recollapsed via the same rotary mechanism and a drawstring, effectively trapping any filtered particulates so that they may be removed with the device. However, the Reger device does not include any provision for dealing with the accumulation of clots and debris over longer time scales. Therefore, the Reger device is not ideal for use to reduce the risk of strokes and embolisms by filtering a patient's blood over longer periods of time.

Vascular filters have been developed for more long term use as well. The Greenfield vena cava filter is representative of this class of devices. The Greenfield vena cava filter is a small metal device designed to protect against a life threatening condition called pulmonary embolism. The Greenfield filter has six metallic legs that are joined together at the top forming a collapsible conical structure. The Greenfield filter can be inserted into a desired location within a patients vein or artery and deployed to expand the conical structure in a manner analogous to that of opening an umbrella. When deployed, the conical structure of the Greenfield filter can be expanded to a size larger than the resting size of the blood vessel, causing it to press against the blood vessel walls to secure it in a desired location.

Other vascular filters have been developed, but these devices all suffer from the drawback that they may become clogged with clots and may, therefore, result in reduced blood flow through the blood vessel being filtered. When these devices become clogged, they typically must be either surgically removed or cleaned via catheterization, procedures which both pose some risk and discomfort to the patient. For example, U.S. Pat. No. 5,626,605 to Irie et al., U.S. Pat. No. 5,984,947 to Smith, and U.S. Pat. No. 6,013,093 to Nott et al., also each disclose devices for insertion into blood vessels to filter clots from a patient's bloodstream. Each of these patents discloses a wire or strut based device that can be attached directly to a blood vessel wall to filter clots. Neither of these devices provide a mechanism to detect and/or dissolve clots. Thus they are less than ideal for use in the long term filtration of clots and debris from a patient's bloodstream.

It can be seen that none of the prior art devices or methods are ideally suited for use to prevent damage due to clot migration in the long term. Therefore, it is desirable to provide a vascular filtration device and method which can be used to filter a patient's blood in the long term and which can also provide for the detection and removal of clots without requiring catheterization or surgical removal.

SUMMARY OF THE INVENTION

Broadly described, the present invention comprises a vascular filtration device for filtering a patient's blood in situ. In a first exemplary embodiment, the vascular filtration device of the present invention includes a channel for being connected to, or inserted within, a patient's blood vessel such that a quantity of blood will flow therethrough. A filter is disposed within the channel for collecting clots and debris in the blood. A sensor is also provided for sensing clot and debris collection by the filter and for generating a signal indicative of the need for injection of an anticoagulant or manual removal of the offending clot(s) or debris collected by the filter.

In a second exemplary embodiment the vascular filtration device includes a chamber housing a strainer which is preferably disposed at an angle to the direction of blood flow to allow accumulation of clots and other debris preferentially at one end of the chamber. The chamber and strainer are preferably both composed of physiologically inert materials such as Teflon, which are similar to those used in other long term implants.

In additional exemplary embodiments, the vascular filtration device may also include a secondary chamber wherein the clots may be retained and dissolved via injection of a clot dissolving compound. An optical or blood pressure sensor can be provided to control the injection of the clot dissolving compound in response to changes in blood optical properties or pressure across the filter resulting from clot accumulation. The sensor can either directly control the injection of the anti-clotting compound or can, alternatively, communicate with a remote monitor to signal the patient or a physician of the need for manual injection of a clot dissolving compound into the retention chamber. In another contemplated embodiment, the sensor includes a transmitter to allow remote monitoring of the measured parameters by a hospital or medical center. In yet another contemplated embodiment, the device includes a hinged opening whereby a catheter may be passed in a particular direction through the device to ensure that the vascular filtration device does not interfere with any necessary catheterization procedures.

The present invention also includes a method for using the vascular filtration device AA to filter blood and/or other bodily fluids flowing through a blood vessel or like passageway. The filtration method of the present invention includes the general steps of: positioning a filter assembly in fluid communication with, or within, a patient's blood vessel; directing a flow of blood through the filter assembly such that the filter assembly acts to retain debris from the blood; and monitoring the accumulation of debris within the filter assembly.

Accordingly, it is an object of the present invention to provide a vascular filtration device which is suitable for long-term use to filter clots and debris from a patient's bloodstream to reduce the risk of strokes and/or pulmonary embolisms.

Another object of the present invention is to provide a vascular filtration device which allows the detection of accumulated blood clots and provides a signal indicative of the need to administer an anti-coagulant or clot dissolving compound.

Still another object of the present invention is to provide a vascular filtration device which will filter clots and debris from patient's blood vessel without precluding the passage of a catheter through the blood vessel.

Other objects, features, and advantages of the present invention will become apparent upon reading and understanding the present specification when taken in conjunction with the appended drawings.

DETAILED DESCRIPTION

The following exemplary embodiments describe the vascular filtration device and method of the present invention and are provided for exemplary purposes and are not meant as limiting the invention.

Figure 1:
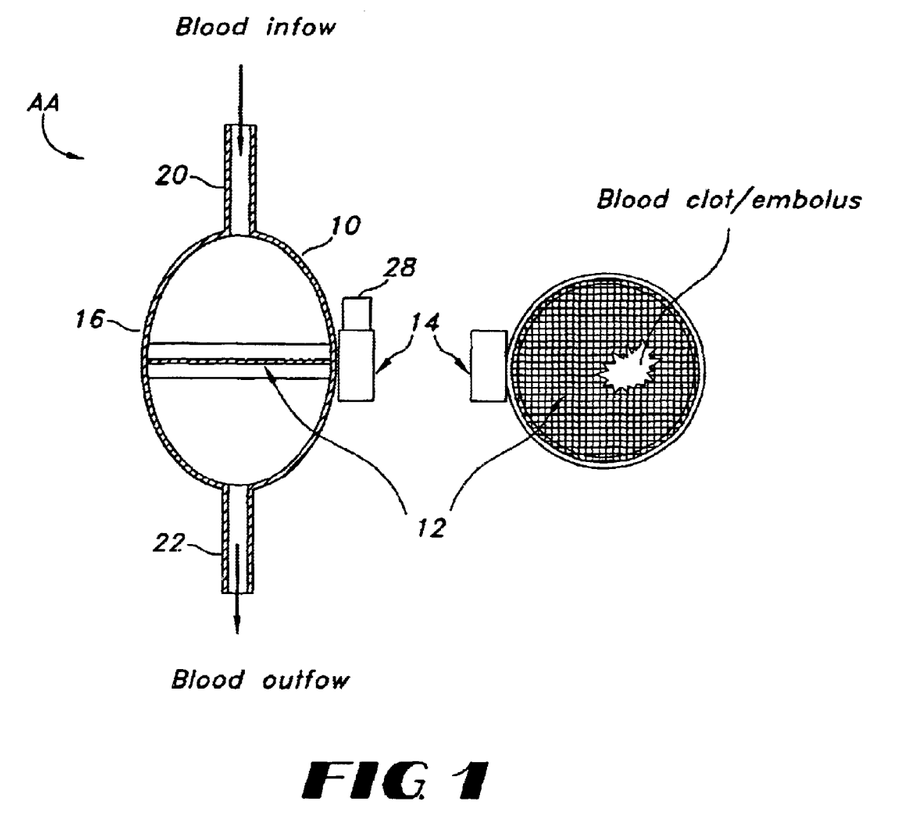
FIG. 1 illustrates a first exemplary embodiment of a vascular filtration device in accordance with the present invention.

Referring now to the drawings in which the numerals represent like components or steps throughout the several views, FIG. 1 displays a first exemplary embodiment of a vascular filtration device AA in accordance with the present invention. Vascular filtration device AA includes a channel 10 that is connectable to a patient's blood vessel such that the blood flow through the vessel passes therethrough. Channel 10 houses a filter 12 which is disposed to remove clots and debris from at least a portion of the blood flowing through channel 10. A sensor 14 may optionally be included to sense the degree to which filter 12 is occluded by clots and debris.

As used herein, the term debris should be taken to encompass any particulate or gelatinous matter being carried through a blood vessel by a patient's blood. For example and not limitation, debris can include such things as: clots, plaque, fatty deposits, bone fragments, cartilage, protein precipitates, or tissue fragments. One of ordinary skill in the art will recognize that the term debris should also include any other particulate or gelatinous matter introduced into the patients bloodstream by bodily trauma, surgery, coagulation, or spalling from the interior wall of blood vessels.

In the exemplary embodiment of FIG. 1, channel 10 includes a chamber 16 having a generally ovoid shape and two connectors 20 and 22. The expanded flow area of chamber 16 allows for filter 12 to have a relatively large surface area in comparison to the diameter of the patient's blood vessel and, thus, to cause a smaller pressure drop as blood flows through filter 12 than would otherwise be obtainable. Its relatively large surface area also allows filter 12 to retain more clots and debris without becoming undesirably clogged to raise blood pressure across the vascular filtration device AA or worse, to completely prevent the passage of blood. It should be obvious to one of ordinary skill in the art that chamber 16 is not limited to an ovoid shape but can also have a number of other shapes, such as, for example and not limitation: a spherical shape, a solid polygonal shape, a cylindrical shape.

Connectors 20 and 22 are provided for facilitating the interconnection of channel 10 to a patient's blood vessel in an intrusive method by severing the blood vessel and inserting connectors 20 and 22 into the upstream and downstream halves of the severed vessel. Preferably connectors 20 and 22 include cylindrical tubes extending from the upstream and downstream ends of channel 10 which are sized to be larger than the natural size of the blood vessel. Thus, when inserted into the blood vessel, connectors 20 and 22 stretch the vessel wall, causing it to tightly grip connectors 20 and 22, thereby holding vascular filtration device A in a desired position. Optionally, a securing band or adhesive may be used to further ensure the secure attachment of vascular filtration device AA to the blood vessel.

Figure 2:
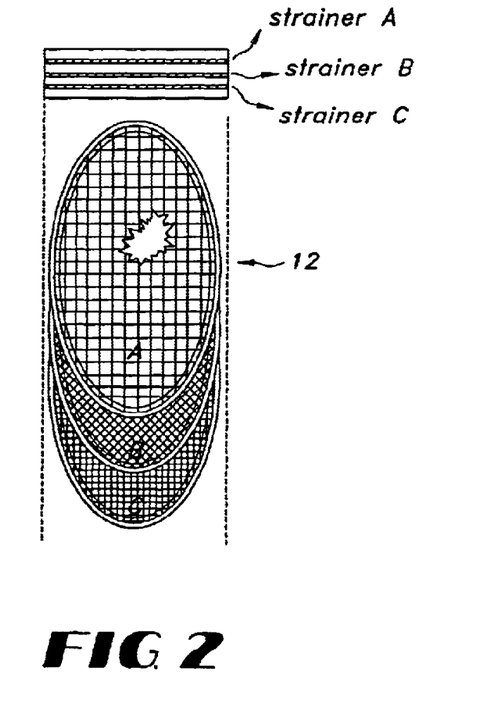
FIG. 2 illustrates a staged filter suitable for use in the first exemplary embodiment of the present invention.

In the first exemplary embodiment, filter 12 is illustrated as a simple wire mesh strainer positioned perpendicular to the blood flow through chamber 16. Filter 12 is preferably made from a physiologically inert material such as stainless steel, plastic, Teflon® or nylon which provides strength and does not induce thrombosis. In an optional embodiment (as shown in FIG. 2) filter 12 may include a filter assembly 24 having two, three, or more filters staged in progressively smaller mesh sizes. For example, the first filter might have a mesh opening size in the range of ¼ to ½ inch, the next 1/16 to ½ inch, and the final filter in the size range of 100 µm to 1/16 inch. The filter mesh should not be so small that it collects or damages white or red blood cells, for example, or unduly increases the blood pressure across the vascular filtration device AA.

In the first exemplary embodiment, sensor 14 is preferably a differential pressure sensor for detecting a differential pressure drop across filter 12 as a result of clogging of filter 12 by clots and debris. Sensor 14 preferably includes a signal generator for generating a clot indicating signal when clots have accumulated on the surface of filter 12 or within channel 10. Sensor 14 is preferably powered by a long-lasting battery, preferably a lithium battery, with a possible lifespan of 5–15 years, or by a plutonium battery having a possible lifespan of 20 to 40 years. Sensor 14 may also include an optical sensor, a flow sensor, or any other conventional sensor capable of directly detecting the presence of clots on the surface of filter 12 and within channel 10.

Sensor 14 preferably includes any conventional pressure sensor which is adaptable to use within a human body. It is not necessary for sensor 14 to actually sense the exact value of the differential pressure across filter 12. Instead, all that is required is that sensor 14 be functional to detect an increase in the differential pressure beyond a preselected maximum value. Accordingly, in the first exemplary embodiment, sensor 14 may include a simple over-pressure transducer for detecting an increase in the pressure drop across filter 12 due to clot accumulation thereon. Pressure transducers of this sort are often used in internal devices adapted to measure physiological blood pressure.

Alternatively, sensor 14 may include a pressure transducer capable of actually returning a measured differential pressure value. An example of a pressure transducer potentially suitable for use in the present invention is illustrated in U.S. Pat. No. 5,357,807 to Gluckel. Gluckel discloses a microminiature semiconductor based pressure transducer which includes a membrane spanning and sealing a cavity on a surface of a semiconductor substrate. Channels extend through the substrate to remote locations (either side of filter 12 when used in the current invention) to establish a pressure differential across the membrane dependent upon the relative pressures at the remote locations. The membrane deflects as differential pressure increases, causing a change in the electrical properties of the membrane and substrate which may be correlated to the differential pressure.

In the exemplary embodiment, sensor 14 is operationally connected to a radio frequency (RF) transmitter 28 capable of generating a short range radio signal indicative of the presence of clots. RF transmitter 28 may be powered by the same long term battery as sensor 14 since it will generally be inactive absent the detection of accumulated clots by sensor 14. One of ordinary skill in the art should recognize that a large number of miniature radio transmitters are readily available which would be easily adaptable to serve the function of RF transmitter 28.

In the first exemplary embodiment, the signal generated by RF transmitter 28 is detected by a receiver carried by the patient or kept in the vicinity of the patient. Receiver is preferably a small device similar to a pager that will activate an audible, visual or tactile alarm to alert the patient upon receipt of a clot detection signal. Alternatively, receiver may instead include a secondary transmitter or hard wired connection for relaying information indicative of a detected clot directly to medical personnel as an indication that an anticoagulant or clot dissolving drug should be injected to dissolve the clots. Again, one of ordinary skill in the art will recognize that a wide variety of radio receivers and transmitters are readily available that would be easily adaptable to serve these functions.

Figure 3:
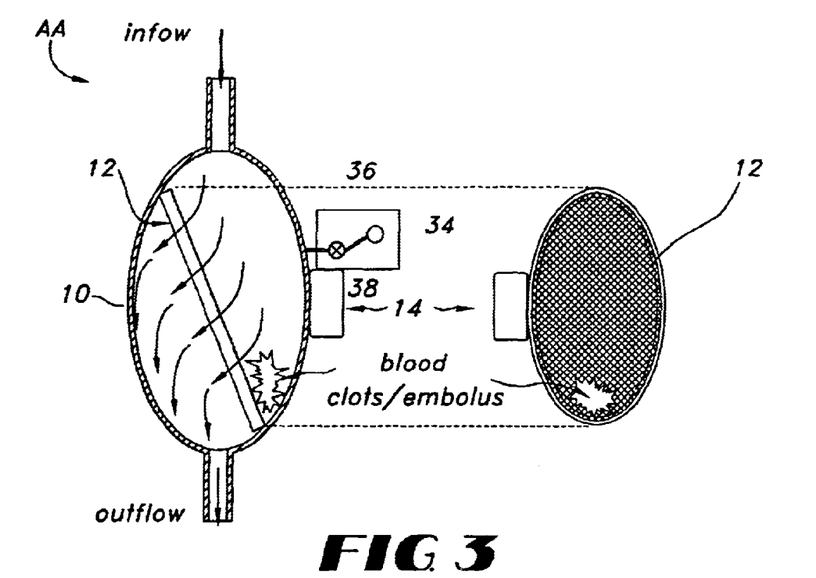
FIG. 3 illustrates a second exemplary embodiment of a vascular filtration device in accordance with the present invention.

As shown in FIG. 3, in a second exemplary embodiment, the clot detection signal may be used to trigger the automatic injection of an anticoagulant or clot dissolving drug directly into chamber 16 by an injector 34. Injector 34 preferably includes a anticoagulant storage reservoir 36 and a gate valve 38. Preferably, injector 34 is positioned adjacent the skin of the patient to allow for easy access and replenishment of anticoagulant into storage reservoir 36 as necessary. Injector 34 may also include a micropump mechanism, such as a rotary motor driving a small positive displacement pump, to force the injection of anticoagulant from storage reservoir 36 into the patient's blood stream. In the exemplary embodiment, subdermal injector 34 is disposed to dispense anticoagulant directly into channel 10 to help dissolve the clot or debris.

Also as illustrated in the second exemplary embodiment of FIG. 3, filter 12 may be positioned at an oblique angle across channel 10, resulting in a larger surface area for clot accumulation. In this configuration the flow of blood against the angled filter 12 tends to cause clots to migrate to the downstream end of the filter 12 and channel 10, where they may be retained without disrupting the flow of blood through filter 12. This serves to keep the majority of filter 12's surface free for blood flow, even when a significant amount of clots or debris have been retained.

Figure 4:
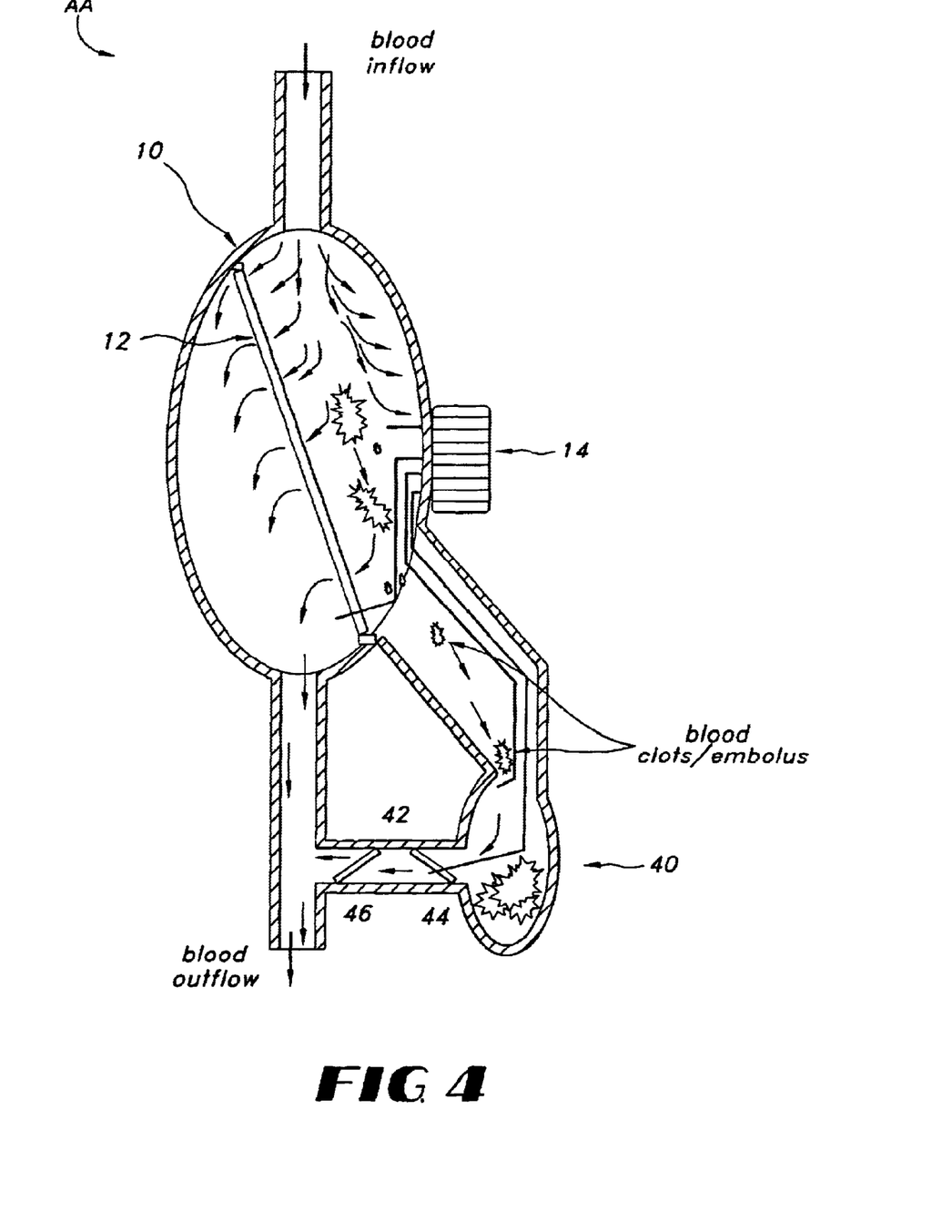
FIG. 4 illustrates a third exemplary embodiment of a vascular filtration device in accordance with the present invention.

FIG. 4. illustrates a third exemplary embodiment of a vascular filtration device AA including a clot retention reservoir 40 disposed on the upstream side of filter 12 but beyond the upper angled edge (relative tot he direction of blood flow) of filter 12. Clot retention reservoir 40 is a chamber disposed to receive clots and debris directed off of the far surface of filter 12, relative to the direction of blood flow, by the impingement of blood flow at an angle to the surface of filter 12. Optionally, as shown, clot retention chamber 40 may include a bypass channel 42 to establish a flow path into and through clot retention reservoir 40 to help direct clots and debris from the surface of filter 12 into clot retention reservoir 40. Preferably bypass channel 42 includes a secondary coarse strainer 44 and microfilter 46 for preventing the escape of any clots from clot retention reservoir 40 back into the patient's blood stream.

Figure 5:
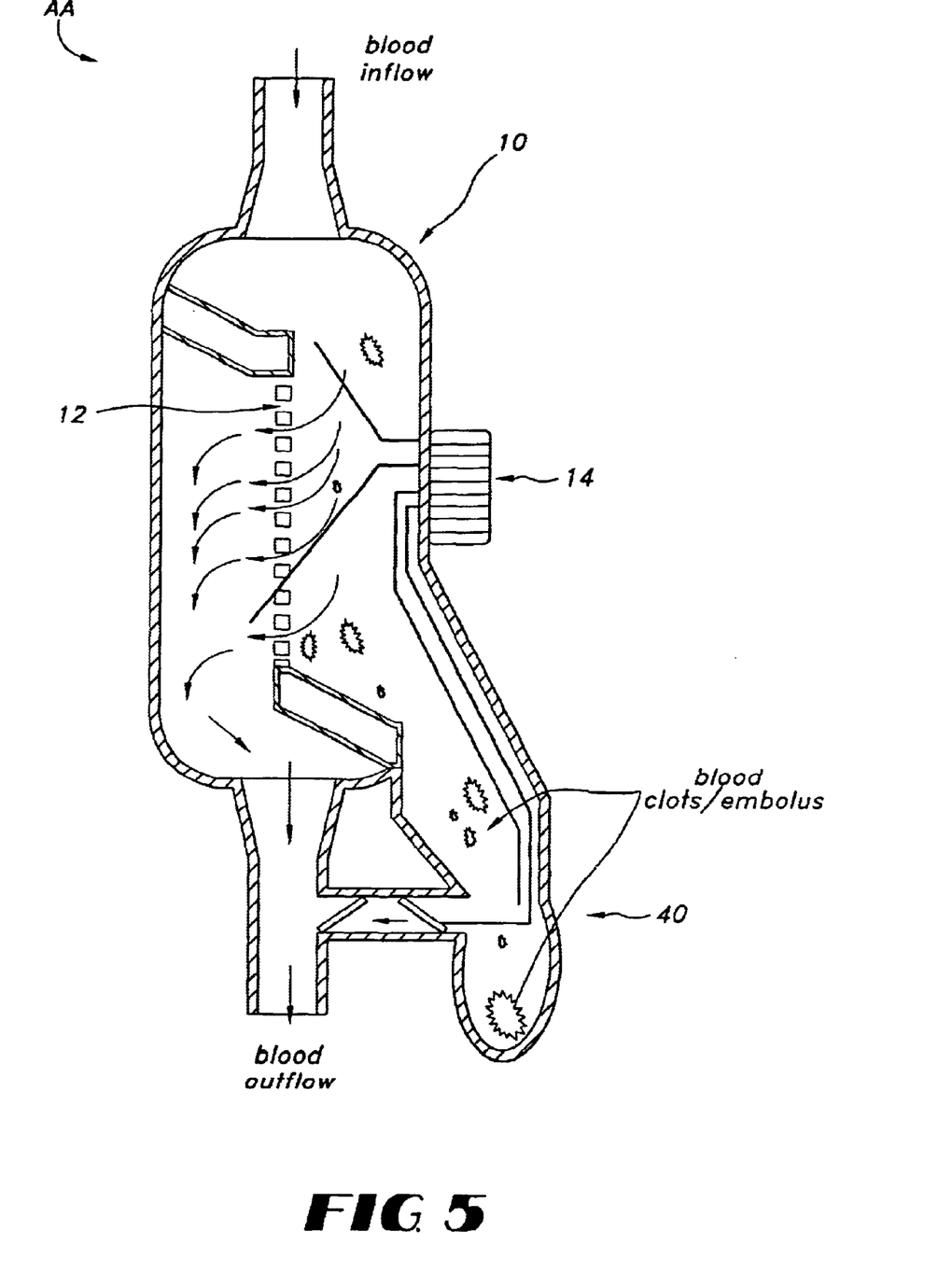
FIG. 5 illustrates a fourth exemplary embodiment of a vascular filtration device in accordance with the present invention.

FIG. 5 illustrates a fourth exemplary embodiment of the vascular filtration device having the same basic design chamber design as the third illustrative embodiment, but with the filter 12 disposed vertically in line with the blood flow through the patient's blood vessel.

Figure 6:
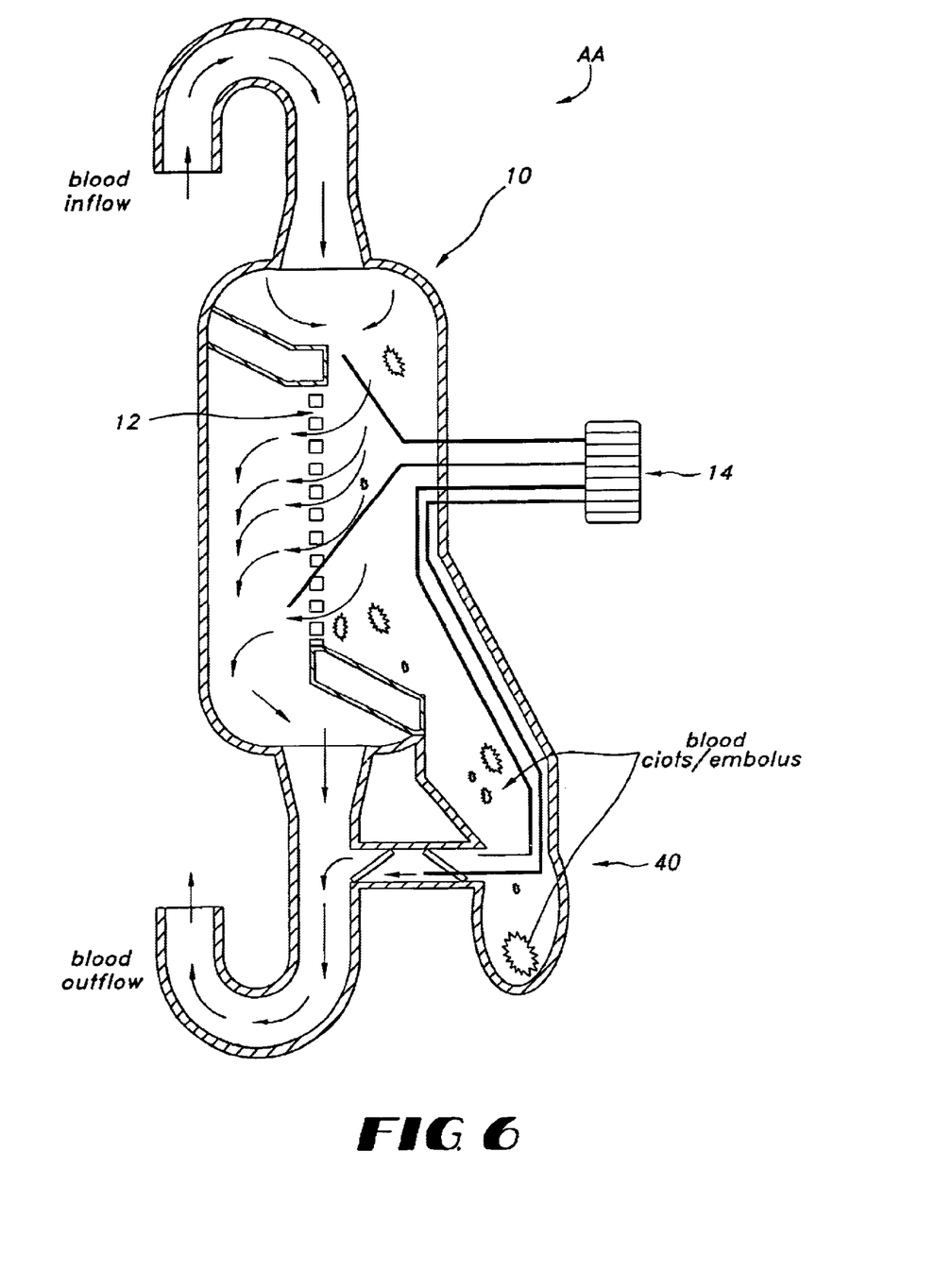
FIG. 6 illustrates a fifth exemplary embodiment of a vascular filtration device in accordance with the present invention.

As shown in FIG. 6 in a fourth exemplary embodiment of vascular filtration device AA may be positioned to incorporate a downwardly directed blood flow, even in an upwardly directed blood vessel. This downwardly directed blood flow is useful to ensure that gravity works to keep the clots within clot retention reservoir 22. As can be seen in FIG. 6, by incorporating 180 degree bends into connectors 20 and 22, vascular filtration device AA is easily positionable in a desired orientation for allowing a downward blood flow therethrough even in an upwardly directed blood vessel to collect debris on the underside of filter 12.

Figure 7:
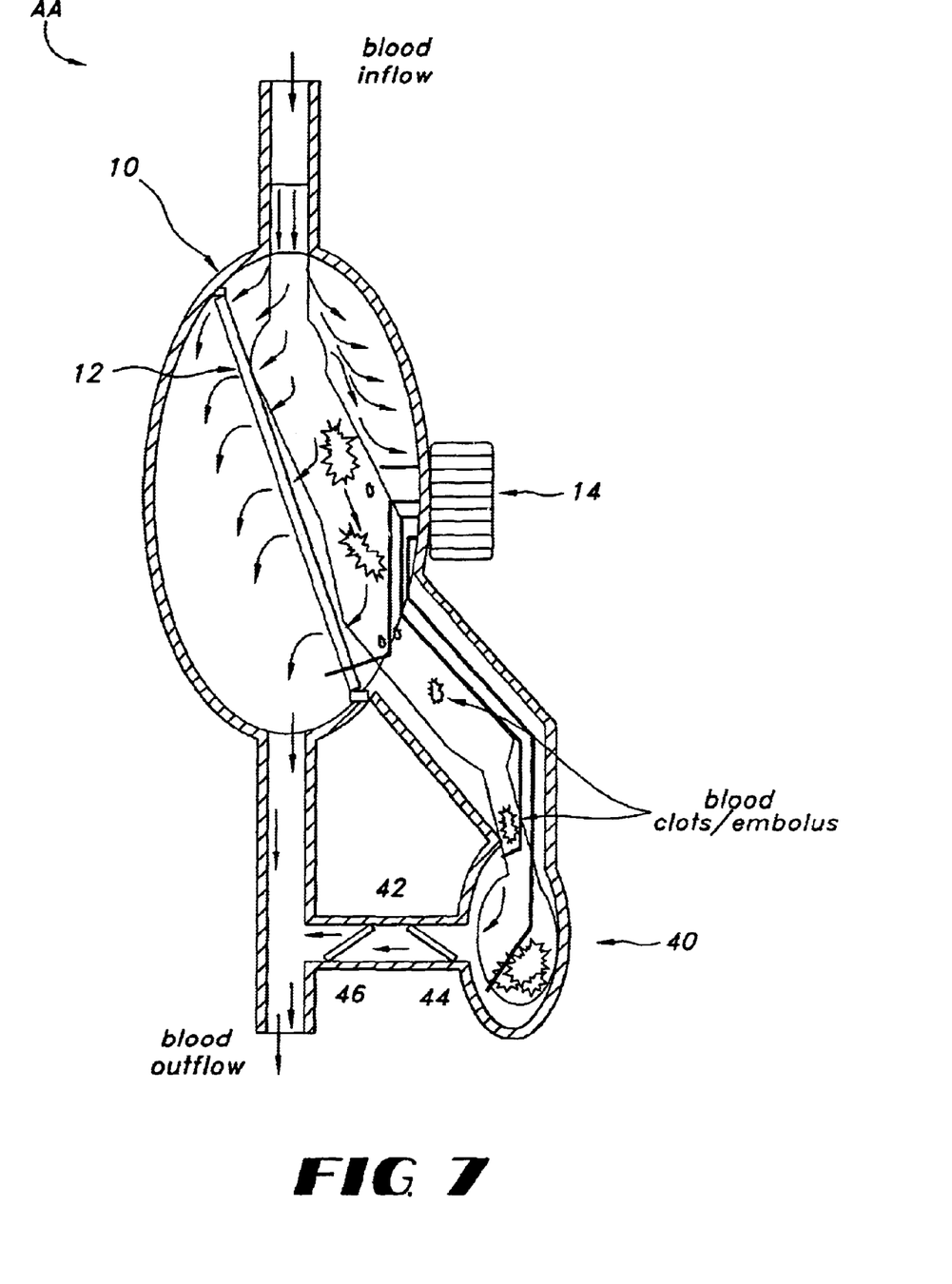
FIG. 7 illustrates a sixth exemplary embodiment of a vascular filtration device in accordance with the present invention.

As shown in FIG. 7, in a fifth exemplary embodiment, a vascular filtration device AA includes a coarse net 52 disposed at the inlet of channel 10 to serve as a pre-filter to prevent the undesirable accumulation of large clots and debris on filter 12. Coarse net 52 is preferably constructed from a physiologically inert woven mesh with a pitch that can be sized to accumulate only larger clots. As shown, coarse net 52 may extend fully into clot retention reservoir 40 or may optionally be positioned just above the location of filter 12.

Figure 8:
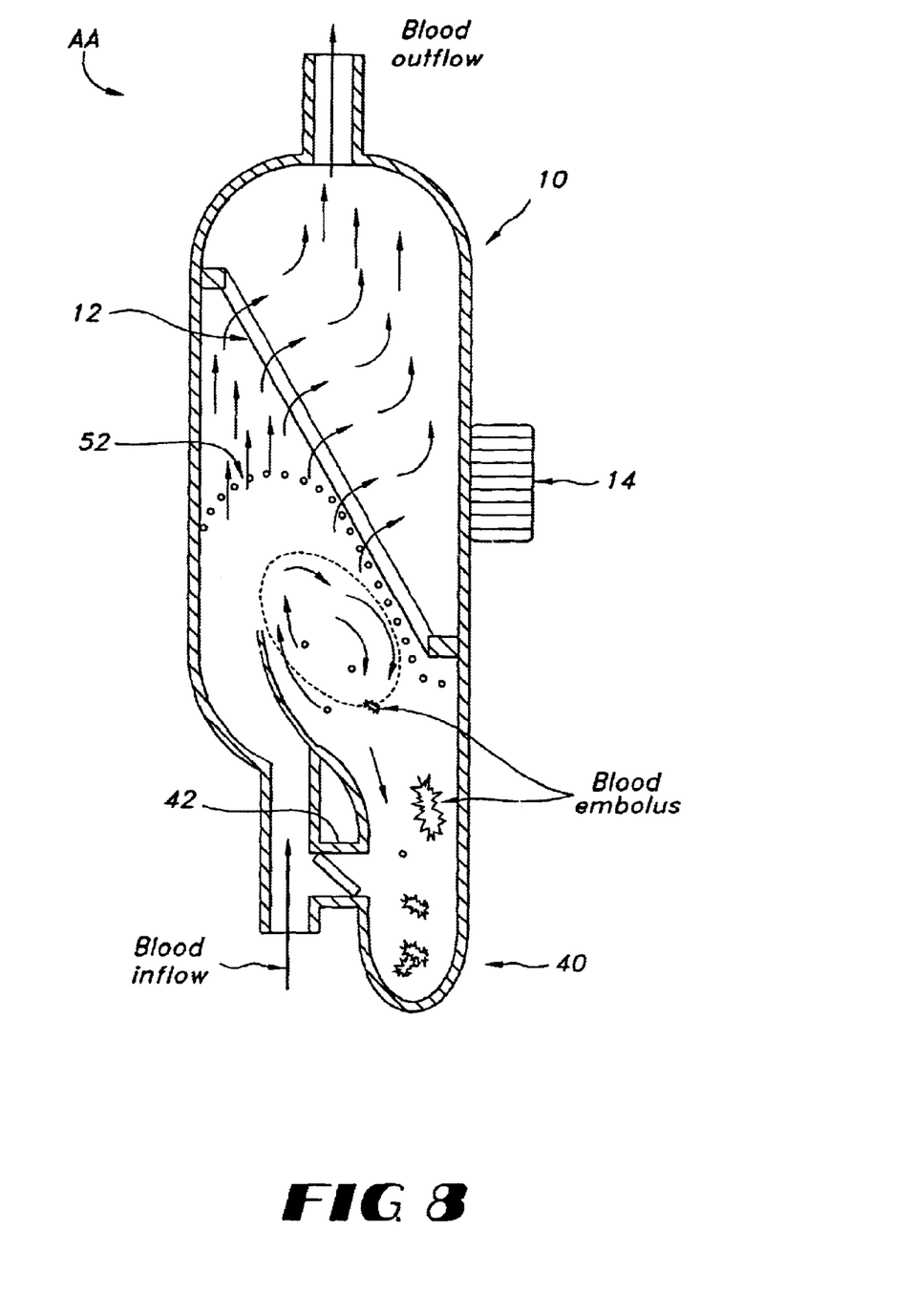
FIG. 8 illustrates a seventh exemplary embodiment of a vascular filtration device in accordance with the present invention.

FIG. 8 illustrates a sixth exemplary embodiment of the vascular filtration device for use in a blood vessel having an upwardly directed blood flow. In this embodiment, blood enters the lower portion of channel 10 and an initial filtration is provided by coarse net 52 to trap large clots and emboli and direct them, in part via the flow of gravity, to a clot retention reservoir 40. As in the previous embodiments, clot retention reservoir 40 includes a bypass or return flow channel 42 for establishing a flow through clot retention reservoir 40. Because the effluent from clot retention reservoir 40 is being recirculated into channel 10, it is not necessary to provide a filter on the flow return channel, although a secondary strainer may optionally be included as shown. Once the blood has been initially filtered by coarse net 52, it next passes through filter 12 and into the upper portion of channel 10 before being reintroduced into the patient's blood vessel.

Figure 9:
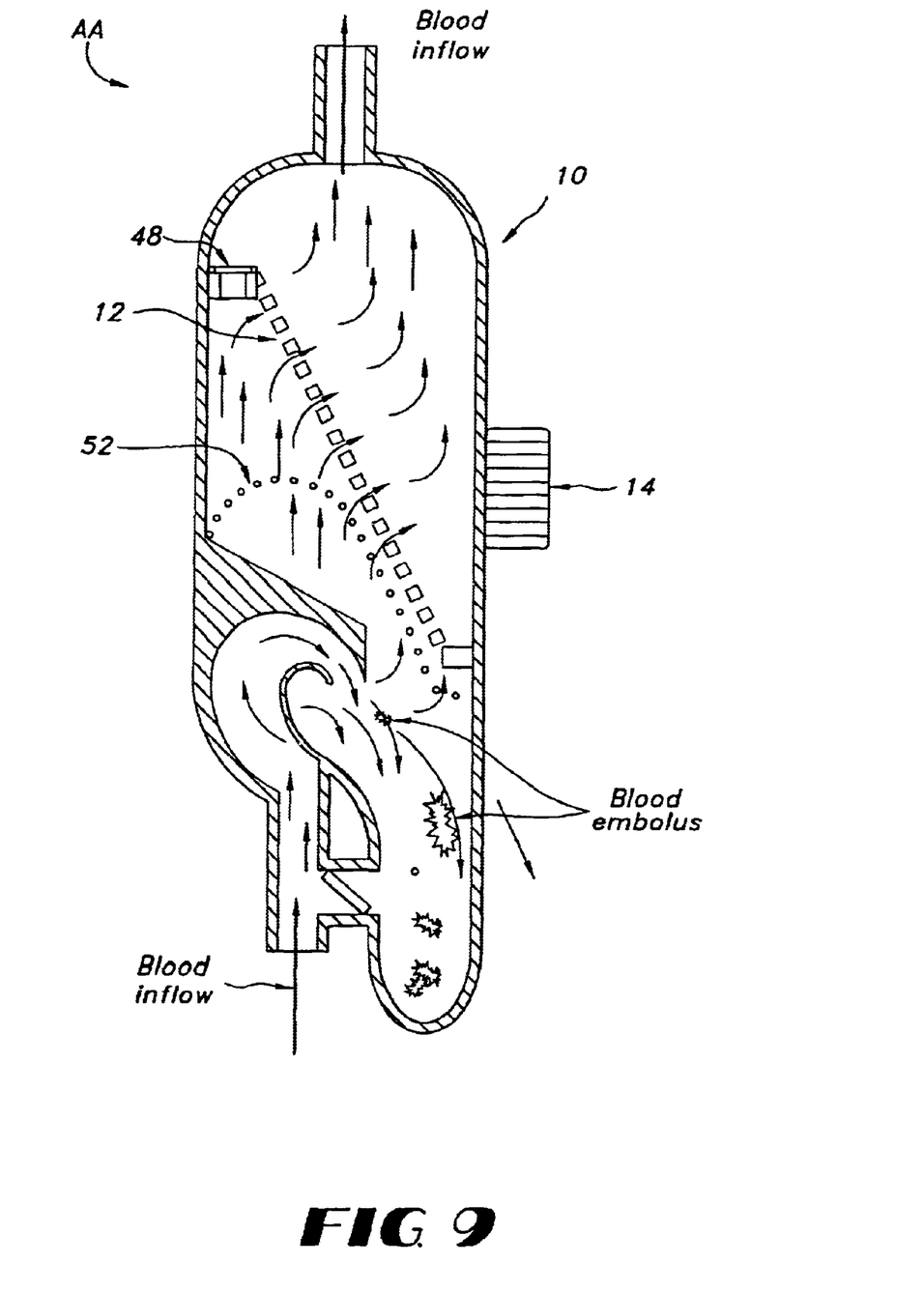
FIG. 9 illustrates an eighth exemplary embodiment of a vascular filtration device in accordance with the present invention.
Figure 10:
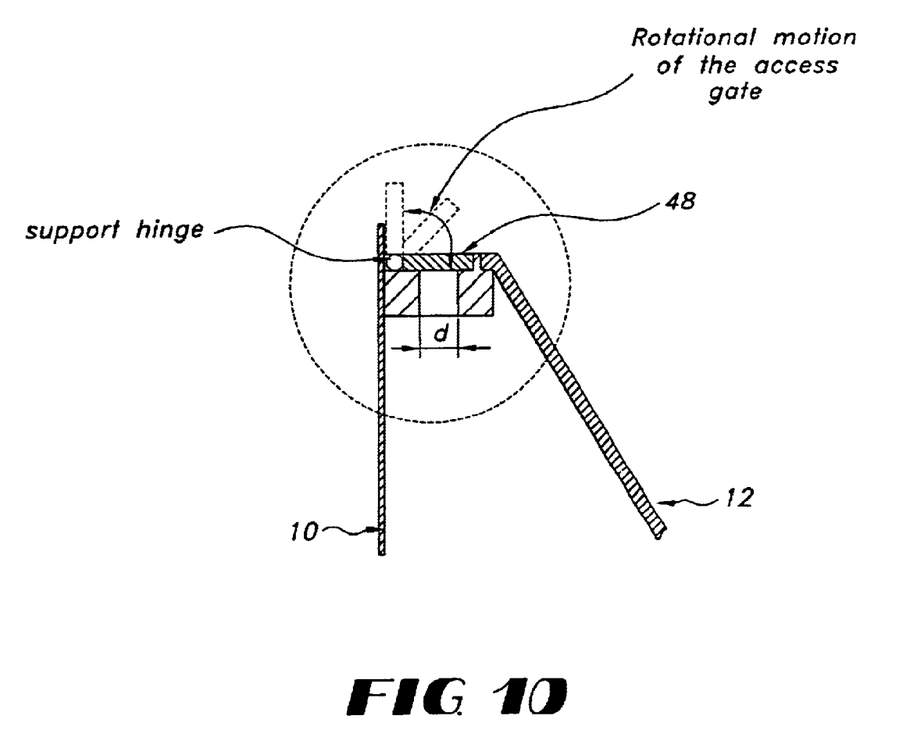
FIG. 10 illustrates close up view of a catheter access gate in accordance with the eighth exemplary embodiment of the present invention.

As illustrated in FIG. 9, in a seventh exemplary embodiment, vascular filtration device AA may be adapted to include a catheter pass-through gate 48 for allowing a catheter to be inserted through and beyond vascular filtration device AA during through gate 48 is a simple one-way hinged gate through which a catheter can pass. FIG. 10 shows a close up view of an exemplary catheter access gate positioned on an inset at one end of filter 12 adjacent the outer wall of chamber 16. Catheter access gate 48 is preferably sized to have a diameter slightly larger than that of the catheter that is intended to be passed therethrough. Those of ordinary skill in the art will recognize that a variety of other check valve or one-way gate type devices could also be used in place of the hinged catheter access gate 48 show in this exemplary embodiment. Additionally, although the catheter access gate 48 shown in FIG. 9 is positioned for use in blood vessel having an upwardly directed flow, it should be recognized that similar catheter access gates 48 may be positioned as needed to allow use in embodiments adapted for use in blood vessels having a downwardly directed flow as well.

Figure 11:
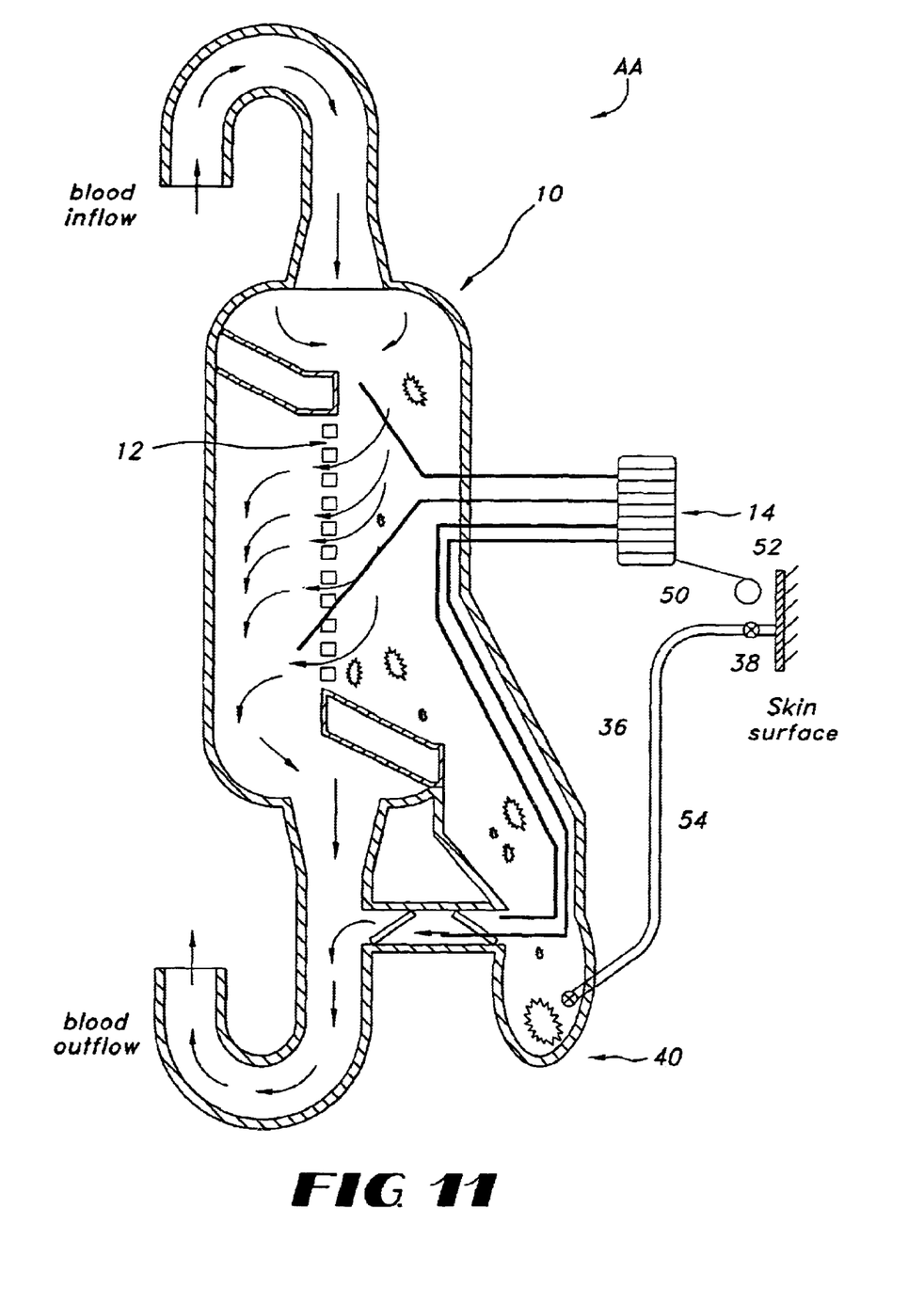
FIG. 11 illustrates an ninth exemplary embodiment of a vascular filtration device in accordance with the present invention.

Also shown in FIG. 11, vascular filtration device AA may include an injection line 36 for allowing a physician to inject anticoagulants or clot-dissolving drugs into channel 10. Injection line 36 is preferably includes a thin piece of physiologically inert tubing that extends from channel 10 to a subcutaneous location adjacent the patient's skin for allowing easy access. A first end of injection line 36 is maintained in fluid communication with channel 10 and the second end at the subcutaneous location comprises an entry port for allowing the administration of liquids into injection line 36. Injection line 36 preferably further includes a one-way valve 38, such as a check valve, for preventing back flow of blood from vascular filtration device A to the entry port. A physician may use injection line 36 to inject drugs or clot dissolving reagents into vascular filtration device AA by simply injecting them into injection line 36 at its end near the patient's skin.

The embodiment shown in FIG. 11 may also optionally conductive wire 50 for facilitating the recharge of the battery powering sensor 14. In this instance, a subcutaneous induction coil 62 may be positioned just below the patient's skin to allow the transcutaneous transfer of electrical power via electromagnetic induction. Similar devices are know in the art and should be easily adaptable to use in conjunction with vascular filtration device AA.

Further, an optional optical fiber 54 may be included for allowing the remote viewing, via fiber optic methods, of the interior of channel 10 and the surface of filter 12. Optical fiber 54 is preferably a high quality optical such as those used for remote viewing of interior structures during surgical and catheterization procedures. A first end of optical fiber 54 is preferably disposed within channel 10 and the opposite end may be planted just below the patient's skin to allow easy access via a small incision when it is necessary to view the interior of channel 10 to inspect for clot accumulation. Optionally, any power source, microprocessor, and/or transmitter subcomponents of sensor 14 may also be positioned remotely, adjacent the skin, and connected to the in situ pressure transducer via conductive wires or optical fibers. Remote placement of sensor subcomponents can reduce the volume required to house sensor 14 at or within channel 10 and can serve to potentially facilitate the positioning of vascular filtration device AA via catheterization.

Figure 12:
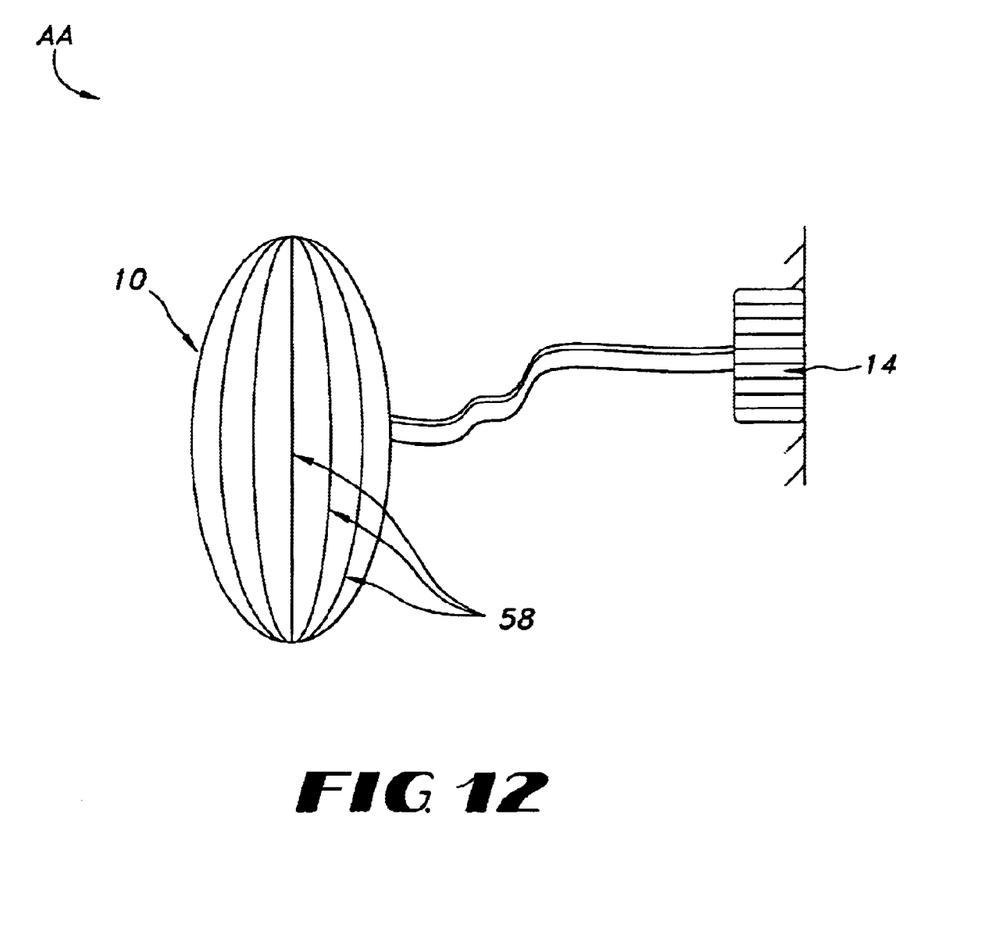
FIG. 12 illustrates an tenth exemplary embodiment of a vascular filtration device in accordance with the present invention.

In an alternative embodiment shown in FIG. 12, vascular filtration device AA may be planted non-obtrusively into the blood vessel via catheterization in a manner somewhat analogous to that used for balloon angioplasty or implantation of a Greenfield Filter. The planting method is based on the use of a catheter to plant the vascular filtration device AA inside the blood vessel at the desired location. In this case, channel 10 is preferably constructed from a flexible material that may be folded and compacted into a small enough volume to be inserted through the blood vessel with a catheter. Additionally, in this embodiment, the walls of channel 10 are preferably constructed from a porous material having a pore size great enough to allow the passage of blood cells without undue shearing in order to allow blood to reach the capillaries and/or lateral blood vessels which would otherwise be occluded by the walls of channel 10.

In the catheter based embodiment, channel 10 is inflatable in a manner similar to balloon angioplasty or may be mechanically deployed in a manner similar to a Greenfield filter. Preferably, channel 10 is prevented from recollapsing by adding stiff wires 58 which spring out to their natural shape upon deployment of vascular filtration device AA from an initial coiled or compressed state which allows them to be passed through the blood vessel via catheterization. Upon inflation, the wires unbend and resume their uncoiled structure, serving to support the flexible walls of channel 10.

The present invention also includes a method for using the vascular filtration device AA to filter blood and/or other bodily fluids flowing through a blood vessel or like passageway. The filtration method of the present invention includes the general steps of: positioning a filter assembly in fluid communication with, or within, a patient's blood vessel; directing a flow of blood through the filter assembly such that the filter assembly acts to retain debris from the blood; and monitoring the accumulation of debris within the filter assembly.

More specifically, a patient's blood can be filtered according to the method of the present invention by positioning a vascular filtration device AA as described heretofore in detail within a patient's blood vessel. The vascular filtration device AA can be positioned and secured to a patient's blood vessel by either of two basic methods: intrusive splicing and grafting onto the blood vessel or implantation via a catheter.

In the intrusive splicing and grafting method, the desired blood vessel is severed at the location wherein it is desirable to insert the vascular filtration device, for example in a patient's vena cava or carotid arteries. Connectors 20 and 22 are then each inserted into the respective appropriate end of the severed blood vessel such that the upstream side of filter 12 receives blood from the blood vessel supplying blood and the downstream side faces the receiving vessel. Connectors 20 and 22 may be secured by stretching the ends of the blood vessel around the connectors as the connectors are inserted into the blood vessel ends. Optionally, connectors 20 and 22 can be secured to the respective blood vessel ends with an adhesive, tensioning bands, or some other known method for grafting devices into blood vessels. Once installed, filter 12 of vascular filtration device AA acts to remove clots and other debris from the patient's blood stream, protecting sites down stream from undesirable clot accumulation which could cause a stroke, embolism or even heart attack.

In the catheterization method, vascular filtration device AA is positioned nonobtrusively into the blood vessel via catheterization in a manner somewhat analogous to that used for balloon angioplasty or for implantation of a Greenfield Filter. In this method, vascular filtration device AA is inserted via a catheter into the patient's blood vessel at a convenient location and delivered by the catheter to the desired filtration location. Once in position, vascular filtration device AA is inflated to a size larger than the normal interior diameter of the blood vessel in a manner similar to balloon angioplasty or may be mechanically deployed in a manner similar to a Greenfield filter. Preferably, channel 10 is prevented from recollapsing by adding stiff wires 58 which spring out to their natural shape upon deployment of vascular filtration device AA from an initial coiled or compressed state which allows them to be passed through the blood vessel via catheterization. Upon inflation, the wires unbend and resume their uncoiled structure, serving to support the flexible walls of channel 10. Because the resulting structure is larger than the resting diameter of the blood vessel, vascular filtration device AA is held firmly in position by the walls of the blood vessel.

In those exemplary embodiments wherein vascular filtration device includes an angled filter and/or a clot retention reservoir 40, the blood flow through vascular filtration device AA and/or gravity may act to move clots from the filter surface into a desired clot retention area. For example, in the second exemplary embodiment, the cross component of the blood flow against the angled filter 12 results in accumulation of clots on the downstream edge of the filter. In those embodiments having clot reservoirs, either the cross flow, or any flow established through bypass channels around filter 12 also serves to direct clots into the clot retention reservoir and to retain them until they can be dealt with.

The method of the present invention also desirably includes the step of detecting clot accumulation by filter 12 and channel 10 using a sensor 14 as heretofore described. Preferably sensor 14 measures the differential pressure across filter 12, although sensor 14 may sense clot accumulation by any other known direct or indirect method including but not limited to measuring optical changes relating to clot accumulation or the reduction in blood flow rate through vascular filtration device AA. When sensor 14 detects a desired threshold clot accumulation level, sensor 14 then generates a clot accumulation signal.

In the first exemplary embodiment, the clot accumulation signal is relayed to RF transmitter 28 which in turn generates a RF signal indicative of clot accumulation. The RF signal is preferably a low power, short range signal which can be detected by a radio receiver carried by or kept in the vicinity of the patient. In its simplest embodiment, the receiver simply alerts to patient to the clot accumulation, indicating that the patient should seek the attention of qualified medical practitioners. Alternatively, the receiver may itself communicate the patient's condition to medical professionals at a remote location via either a wireless or hard wired connection.

As shown in the second exemplary embodiment, when vascular filtration device AA also includes an injector 34 for injecting an anticoagulant of clot-dissolving compound, the clot accumulation signal generated by sensor 14 may also trigger the automatic release of an anticoagulant or clot-dissolving compound directly into channel 10. Alternatively, as shown for example in the ninth exemplary embodiment, medical professionally may manually inject the anticoagulant into vascular filtration device AA via injector lines which terminate just under the patient's skin, or may even just inject the anti-coagulant into the patient's bloodstream directly as with an normal vaccination or injection. Also, if an optical fiber is present for allowing inspection, as in the ninth embodiment, the medical professionals may access the fiber by incising the skin overlying the fiber and by connecting a remote optical viewer to the subcutaneous end of the fiber to allow remote viewing of the interior of channel 10 through the optical fiber.

The ninth exemplary embodiment shown in FIG. 11, also optionally allows for the remote recharging of the battery powering sensor 14 via conductive wire 50 and subcutaneous induction coil 62 via the use of a transdermal inductive current. This can be accomplished by applying the magnetic field from an alternating current based power source to a coil external to the patient's skin adjacent to subcutaneous induction coil 62. The alternating current induces a current in subcutaneous induction coil 62 which can be rectified and used to charge the battery powering sensor 14. Similar devices and procedures are known in the art and should be easily adaptable to this application.

Further, the interior of channel 10 may be viewed remotely using optical fiber 54 using traditional fiber optic methods. For remote viewing, the end of optical fiber 54 planted adjacent the patient's skin is accessed by making small incision and connected to a fiber viewer. The physician may then observe remotely an image of the interior of channel 10 to inspect for the accumulation of clots and other debris in determining a course of treatment.

While the aforementioned embodiments have been described primarily in the context of providing a method of filtering a patient's blood, it should be easily recognizable that the vascular filtration device is also adaptable to filter almost any bodily fluid which is transported in ducts, tubules or other bodily fluid transport passageways. For example, the device of the present invention could also be utilized to prevent the escape of kidney stones into a patient's urinary tract or the movement of gall stones from a patient's gall bladder.

The foregoing description has been presented for purposes of illustration and description. It is not intended to be exhaustive or to limit the invention to the precise forms disclosed. Obvious modifications or variations are possible in light of the above teachings. The embodiments discussed, however, were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention, as determined by the appended claims when interpreted in accordance with the breadth to which they are fairly and legally entitled. Additionally, the many additional embodiments illustrated and described in the accompanying materials should be considered a part of the present invention.

What is claimed is:

1. A vascular filtration device comprising:
   an expandable channel having a porous exterior surface, wherein said channel is designed to be positioned within a bodily fluid transport passageway and in fluid communication with said bodily fluid transport passageway to allow the passage of a quantity of said bodily fluid through said channel;
   a filter for collecting debris from said quantity of bodily fluid, wherein said filter is disposed within said channel such that at least a portion of said bodily fluid must flow through said filter; and
   a sensor for sensing the accumulation of debris by said filter and in said channel.

2. The vascular filtration device of claim 1, wherein said bodily fluid is blood.

3. The vascular filtration device of claim 1, wherein said channel also includes a debris retention chamber in fluid communication with said channel.

4. The vascular filtration device of claim 3, wherein said filter is disposed at an oblique angle to said flow of said bodily fluid, thereby resulting in a flow across said filter to direct debris into said debris retention chamber.

5. The vascular filtration device of claim 3, wherein said debris retention chamber is disposed upstream of and gravitationally below said filter, thereby allowing gravity to direct debris into said debris retention chamber.

6. The vascular filtration device of claim 3, further including a bypass channel fluidly connecting said debris retention chamber to said channel at a position downstream of said filter, thereby establishing a flow into and through said debris retention chamber.

7. The vascular filtration device of claim 1, further including a catheter gateway for allowing a catheter to be passed completely through said channel and said filter.

8. The vascular filtration device of claim 1, wherein said channel includes an expansion chamber whereby the surface area of said filter may be increased over what would be possible in a channel having a cross section approximately the same size as the cross section of said bodily fluid transport passageway.

9. The vascular filtration device of claim 1, further including a pre-filter device within said channel upstream of said filter for removing large debris and directing said large debris away from said filter.

10. The vascular filtration device of claim 1, wherein said sensor includes a sensor selected from the group consisting of: a differential pressure sensor, an optical sensor and a flow sensor.

11. The vascular filtration device of claim 1, wherein said sensor includes a transmitter for transmitting information indicative of detected debris accumulation to a remote location.

12. The vascular filtration device of claim 1, further comprising an injector for injecting a quantity of a clot dissolving compound into said channel upon detection by said sensor of the accumulation of a specified amount of debris on said filter.

13. The vascular filtration device of claim 1, further comprising an injection line extending to a location adjacent an exterior surface of a mammal's body, thereby allowing the injection of a clot dissolving compound.

14. The vascular filtration device of claim 1, further comprising an optical fiber extending from the interior of said channel to a location adjacent an exterior surface of a mammal's body, thereby allowing the remote viewing of the interior of said channel.

15. The vascular filtration device of claim 1, wherein said channel is adapted to be connected to a blood vessel.

16. The vascular filtration device of claim 1, wherein said channel is adapted to be positioned within a blood vessel.

17. The vascular filtration device of claim 1, wherein said channel is adapted to be used in a blood vessel having an upwardly directed flow.

18. The vascular filtration device of claim 1, wherein said channel is adapted to be used in a blood vessel having a downwardly directed flow.

19. A method for filtering a bodily fluid flowing through a bodily fluid transport passageway, said method including the steps of:
    positioning the filter assembly of claim 1 in fluid communication with said bodily fluid transport passageway;
    directing a flow of said bodily fluid through said filter assembly such that said filter assembly acts to retain debris from said bodily fluid; and
    sensing the accumulation of debris within said filter assembly.

20. The method of claim 19, further including the step of injecting a clot-dissolving compound into said filter assembly when a threshold debris accumulation is detected.

21. The method of claim 20, further including the step of sequestering said debris within a debris retention chamber prior to injection of said clot dissolving compound.

22. The method of claim 21, wherein said filter assembly includes a filter and further including the step of directing a portion of said bodily fluid laterally along an upstream surface of said filter to direct said debris into said debris retention chamber.

23. The method of claim 21, further including the step of allowing gravity to direct debris into said debris retention chamber.

24. The method of claim 19, further including the step of transmitting information indicative of detected debris accumulation to a remote location.

25. The method of claim 19, wherein said filter assembly includes a coarse mesh bag disposed upstream of said filter for removing large debris and directing said large debris away from said filter.

26. The method of claim 19, wherein said monitoring step includes the step of detecting clot accumulation using a sensor selected from the group consisting of: a differential pressure sensor, an optical sensor and a flow sensor.

27. The method of claim 20, wherein said injecting step includes the step of injecting a clot dissolving compound through an injection line extending from said filter assembly to a location adjacent the surface of a mammal's body.

28. The method of claim 19, wherein said bodily fluid is blood.

29. The method of claim 19, wherein said positioning step includes the step of connecting said channel to a blood vessel.

30. The method of claim 19, wherein said positioning step includes the step of inserting said channel into a blood vessel.

31. The vascular filtration device of claim 1 wherein said channel is collapsible.

32. The vascular filtration device of claim 1 wherein said channel is made from a flexible material.

33. The vascular filtration device of claim 32 wherein said channel is foldable to permit insertion though the bodily fluid passageway with a catheter.

34. The vascular filtration device of claim 1 wherein said channel is inflatable.

35. The vascular filtration device of claim 1 wherein said channel is supported by a plurality of elongated and outwardly biased wires.

36. The vascular filtration device of claim 35 wherein said plurality of wires are compressible to permit said channel to pass through the bodily fluid passageway via catheterization.

37. A filtration device or the in situ removal of debris from a bodily fluid, said filtration device comprising:

- a channel in fluid communication with a fluid transport passageway to allow the passage of a quantity of bodily fluid therethrough;
- a first filter for removing debris from said quantity of bodily fluid, wherein said first filter is disposed within said channel such that at least a portion of said bodily fluid flows through said first filter;
- a second filter for removing debris from said quantity of bodily fluid flowing through said first filter, wherein said second filter is disposed downstream of said first filter in said channel; and
- a sensor for sensing the accumulation of debris by said filter and in said channel.

38. The vascular filtration device of claim 31 wherein said channel is made from a porous material having a pore size permitting the flow of blood therethrough.

* * * * *